United States Patent
Edsinger et al.

(10) Patent No.: US 7,388,369 B2
(45) Date of Patent: Jun. 17, 2008

(54) METHOD AND APPARATUS FOR MEASURING HYDROGEN CONCENTRATION IN ZIRCONIUM ALLOY COMPONENTS IN THE FUEL POOL OF A NUCLEAR POWER PLANT

(75) Inventors: Kurt Edsinger, Pleasanton, CA (US); Suresh K. Yagnik, Pleasanton, CA (US); Duane P. Johnson, Loomis, CA (US)

(73) Assignee: Electric Power Research Institute, Inc., Palo Alto, CA (US)

( * ) Notice: Subject to any disclaimer, the term of this patent is extended or adjusted under 35 U.S.C. 154(b) by 262 days.

(21) Appl. No.: 11/001,405

(22) Filed: Nov. 30, 2004

(65) Prior Publication Data

US 2007/0279050 A1    Dec. 6, 2007

(51) Int. Cl.
G01B 7/06 (2006.01)
G01R 33/12 (2006.01)

(52) U.S. Cl. ........................ 324/230; 324/202; 324/228; 376/245

(58) Field of Classification Search ......... 324/219–221, 324/233, 239–243, 202, 228–231; 376/245
See application file for complete search history.

(56) References Cited

U.S. PATENT DOCUMENTS

| | | | |
|---|---|---|---|
| 4,402,904 A | | 9/1983 | Anthony |
| 5,341,678 A | | 8/1994 | Kervinen |
| 5,889,401 A | * | 3/1999 | Jourdain et al. ............. 324/230 |
| 6,366,083 B1 | | 4/2002 | McClelland |
| 6,369,566 B1 | | 4/2002 | McClelland |
| 6,541,964 B1 | * | 4/2003 | Jourdain et al. ............. 324/232 |
| 6,583,618 B2 | * | 6/2003 | McClelland ................ 324/239 |
| 6,640,635 B2 | | 11/2003 | Nakatsuka |

OTHER PUBLICATIONS

"Introduction to Eddy Current Technology, Historical backgrraound and Electrical Theory," http://www.joe.buckley.net/papers/eddyc/ectek2.htm, (Jul. 11, 2003).
"Introduction to Eddy Current Technology, Basic Eddy Current Testing, Pt. 1," http://www.joe.buckley.net/papers/eddyc/ectek3.htm, (Jul. 11, 2003).

(Continued)

*Primary Examiner*—Jay M Patidar
(74) *Attorney, Agent, or Firm*—Kilpatrick Stockton LLP

(57) ABSTRACT

The present invention provides a method for measuring hydrogen concentration in an electrically conductive material, such as a nuclear fuel rod, comprising calibrating an eddy current probe at a plurality of hydrogen concentrations; measuring eddy currents at a plurality of positions along an electrically conductive material; and calculating a hydrogen concentration in the electrically conductive material at each of the positions along the electrically conductive material. The present invention also provides a system for measuring hydrogen concentration in a nuclear fuel rod, comprising an eddy current probe; a nuclear fuel rod calibration standard; a data handling system for collecting data generated by the eddy current probe and for performing calculations using the data. The system may be utilized in-situ and may comprise a movable probe mount configured to hold the eddy current probe and to traverse the calibration standard and the nuclear fuel rod to be measured.

19 Claims, 3 Drawing Sheets

OTHER PUBLICATIONS

"Introduction to Eddy Current Technology, Basic Eddy Current Testing, Pt. 2," http://www.joe.buckley.net/papers/eddyc/ectek4.htm, (Jul. 11, 2003).

"Introduction to Eddy Current Technology, Practical Testing," http://www.joe.buckley.net/papers/eddyc/ectek5.htm, (Jul. 11, 2003).

"Introduction to Eddy Current Technology, Applications," http://www.joe.buckley.net/papers/eddyc/ectek6.htm, (Jul. 11, 2003).

Lois, A., "Eddy current assessment of Hydrogen content in Zirconium based alloys," http://www.ndt.net/article/wcndt00/papers/idn332/idn332.htm, (Mar. 25, 2003).

TWI World Center for Material Joining Technology, "Eddy Current Testing (Jul. 2002)," http://www.twi.co.uk/j32k/protected/band_3/ksndt004.html, (Jul. 2002).

Suresh Yagnik et al., "Eddy Current Measurements of Corrosion and Metal Loss in Zircalloy Cladding with Ferromagnetic Crud," Nuclear Technology, vol. 147, No. 2, Aug. 2004, pp. 291-300.

Yagnik, S., "Eddy Current Measurements of Hydrogen Concentration and Metal Loss in Zircaloy Samples: Phase 1:Feasibility Studies," EPRI, Final Report, Jul. 2001.

International Search Report mailed Mar. 28, 2007 corresponding to PCT/US05/39666.

* cited by examiner

METHOD AND APPARATUS FOR MEASURING HYDROGEN CONCENTRATION IN ZIRCONIUM ALLOY COMPONENTS IN THE FUEL POOL OF A NUCLEAR POWER PLANT

BACKGROUND OF THE INVENTION

1. Field of the Invention

The present invention relates generally to a method of measuring hydrogen concentration in conductive materials. In particular, the present invention relates to a method of measuring hydrogen concentration in nuclear fuel rod claddings using eddy current techniques.

2. Description of the Related Art

The useful lifetime of nuclear fuel rods is limited, in part, by the structural integrity of the zirconium alloy cladding encasing the radioactive material used to power the reactor. One measure of the structural integrity of the zirconium alloy cladding is the hydrogen concentration in the cladding. Hydrogen concentration is important because hydrogen precipitates as a brittle second phase. An average concentration across the cladding wall on the order of 600 parts per million (ppm) leads to measurable hydrogen embrittlement. However, the hydrogen concentration across the wall of the cladding is not uniform. The concentration at the outer surface (OD) of the cladding can be more than ten times higher than at the inner surface (ID) of the cladding, forming an OD rim of brittle second phase. The thickness of this rim depends primarily upon the amount of absorbed hydrogen and the temperature and temperature gradient across the wall during operation. This embrittlement leaves the cladding material susceptible to cracking, potentially leading to release of fissionable material into the reactor coolant. Therefore, determining hydrogen concentration in nuclear fuel rods is of great interest to the nuclear power industry.

The current method for determining hydrogen concentration in nuclear fuel rods is a destructive method, involving cutting samples out of the rod. These samples must be shipped to a laboratory that is equipped to handle radioactive materials for analysis. The analysis is a slow and expensive analytical process, requiring skilled operators and complicated equipment. Consequently, the number of analytical samples processed is relatively small, compared to the total sample population. This leads to a poor statistical representation of the fuel rod population, which may result in premature discharge of fuel rods, or more importantly, may lead to the use of fuel rods past their safe operating lifetime. Therefore, while this method is accurate, the fact that it is destructive, requires off-site analysis, and is slow limits its usefulness.

In-situ methods of hydrogen measurement are available. However, these in-situ methods involve indirect measurements and assumptions which, if untrue, lead to large errors in hydrogen concentration. One such method measures a parameter different than hydrogen concentration, the zirconium oxide thickness, which is then correlated to hydrogen concentration using certain assumptions. Zirconium oxide is formed at the surface of fuel rods in the reaction between the zirconium cladding and the water used as a moderator in light water reactors. During operation of the reactor, the high temperatures at the surface of fuel rods cause the water to react with the surface. The hydrogen left after the oxygen from the water has reacted either absorbs into the cladding or remains in the water. Generally, a significant fraction of the available hydrogen is absorbed by the metal. The zirconium oxide-based analysis proceeds as follows.

The thickness of the zirconium oxide layer is determined using an eddy current probe pressed against the surface of the fuel rod. This technique uses a probe containing a metal coil of wire, excited with radio-frequency alternating current, to induce a current, called an eddy current, in the fuel rod cladding. The induced eddy current in turn induces a back EMF in the probe coil and changes the probe impedance. The induced eddy current and probe impedance are dependent upon how close the probe is to the cladding, the effective electrical conductivity of the cladding, the effective magnetic permeability of any material between the probe and the cladding, and, if the excitation frequency is low enough, the thickness of the cladding. The presence of zirconium oxide, which is a non-magnetic electrical insulator, causes the probe to be separated from the metal cladding surface. The greater the zirconium oxide thickness, the further the probe is from the metal surface and the smaller the induced eddy current. Normally the excitation frequency is high enough such that the induced eddy current does not penetrate to the ID of the fuel rod cladding. The probe impedance is calibrated by using standards of the cladding material with various known thicknesses of insulating material placed between the probe and the cladding surface. Since only the conducting properties of the insulating materials are of importance, the insulating layer used for calibration need not be an oxide. Mylar films, for instance, are commonly used. The calibration curve combined with the in-situ eddy current impedance when the probe is pressed against the fuel rod is assumed to be a measure of the zirconium oxide thickness.

This zirconium oxide thickness measurement, however, is subject to a number of sources of error. First, there is often an additional surface layer, known as crud, formed by agglomeration of coolant corrosion products on the fuel cladding surface. There are many sources of corrosion and wear products in a reactor system, including pumps, piping, and cladding. These products may be small particles of metal oxide from metal surface oxidation or from metal-to-metal contact. The crud is not typically discernable from the zirconium oxide through eddy current methods since it is also a poor conductor, so the assessed oxide thickness is skewed by an amount equal to the thickness of the crud. This results in an erroneously high zirconium oxide thickness measurement. Because hydrogen concentration is correlated directly with zirconium oxide thickness, this also results in an erroneously high estimate of hydrogen level. The overestimation of oxide thickness and hydrogen concentration both lead to a determination that the fuel rods are closer to the end of their useful life than is actually the case. This could potentially lead to premature discharge of fuel rods and wasted money and resources.

A second condition that may be a source of error, related to crud deposition, is when ferromagnetic material is deposited onto the cladding surface. Zirconium oxide is non-magnetic. Deposition of ferromagnetic material onto the surface of zirconium oxide leads to a distortion of the radio frequency energy applied through the probe and a change in the eddy current response, which results in an even greater overestimation of zirconium oxide layer thickness. This error is sometimes corrected using the two dimensional nature of the eddy current response. The correction assumes, however, that fuel rod wall thickness and crud permeability are uniform. Neither of these assumptions is typically true, which leads to errors in estimation of oxide thickness and in hydrogen content. Such assumptions may lead to errors in calibration of 15% or more, depending on the actual circumstances. U.S. Pat. No. 5,889,401 to Jourdain, et al. discloses a refinement to the above approach in which measurements are iteratively fit to a mathematical model of the probe and its interaction with the fuel rod and environment to estimate zirconium oxide and crud thickness. This method has been extended to include measurement of hydride in U.S. Pat. No. 6,541,964, also to Jourdain et al. However, theses methods still do not directly measure the parameter of interest, hydrogen concentration. The former patent is only useful for oxide and crud measurement, while the latter patent still depends on an indirect, iterative, mathematical model approach. In addition, U.S. Pat. No. 6,541,964 does not address a number of key complications, including fuel rod temperature, temperature gradients, and inhomogeneous hydrogen concentrations.

What is needed is a direct method of measuring hydrogen content in nuclear fuel rods. The measurement should preferably be made in-situ and should be independent of the temperature at which the measurement is performed.

SUMMARY OF THE INVENTION

The present invention provides, in one embodiment, a method for measuring hydrogen concentration in an electrically conductive material, comprising calibrating an eddy current probe at a plurality of hydrogen concentrations; measuring eddy currents at a plurality of positions along an electrically conductive material; and calculating a hydrogen concentration in the electrically conductive material at each of the positions along the electrically conductive material.

In one embodiment, the electrically conductive material is a nuclear fuel rod including its cladding. In another embodiment, a calibration standard is used that represents background variables that may affect the eddy current probe response, such as zirconium oxide thickness, ferromagnetic and non-ferromagnetic crud thickness, effective crud permeability, fuel rod temperature and combinations thereof.

The present invention also provides a method for measuring hydrogen concentration in a nuclear fuel rod, comprising calibrating an eddy current probe at a plurality of hydrogen concentrations along a nuclear fuel rod calibration standard disposed within a pool of water; measuring eddy currents at a plurality of positions along a nuclear fuel rod disposed adjacent to the nuclear fuel rod calibration standard in the pool of water; and calculating a hydrogen concentration in the nuclear fuel rod at each of the positions along the nuclear fuel rod.

The present invention also provides a system for measuring hydrogen concentration in a nuclear fuel rod, comprising an eddy current probe; a nuclear fuel rod calibration standard; a data handling system for collecting data generated by the eddy current probe and for performing calculations using the data. In one embodiment, the system may be utilized in-situ and further comprises a movable probe mount configured to hold the eddy current probe and to traverse along a length of the nuclear fuel rod calibration standard and the nuclear fuel rod to be measured.

The method of the present invention is useful for in-situ measurement of hydrogen in nuclear power plant fuel rod claddings. This method eliminates the expense of destructively examining fuel rods. Furthermore, it eliminates uncertainty present with other eddy current methods in which hydrogen concentration is estimated by measurement of cladding oxide thickness.

DETAILED DESCRIPTION OF THE INVENTION

The present invention provides a method for measuring any parameter of interest in a particular sample using an eddy current probe. For example, the probe may be used to measure hydrogen concentration in a piece or section of metal, such as the hydrogen concentration in the cladding of a nuclear fuel rod. Generally, the eddy current probe is calibrated using a calibration standard that provides varying amounts of the parameter of interest in a material or substrate that represents the sample to be measured. For example, the calibration standard may be a piece of metal having varying hydrogen concentrations similar to the piece of metal or sample to be measured. The calibrated probe is then used to measure the parameter of interest in a given sample.

Figure 1:
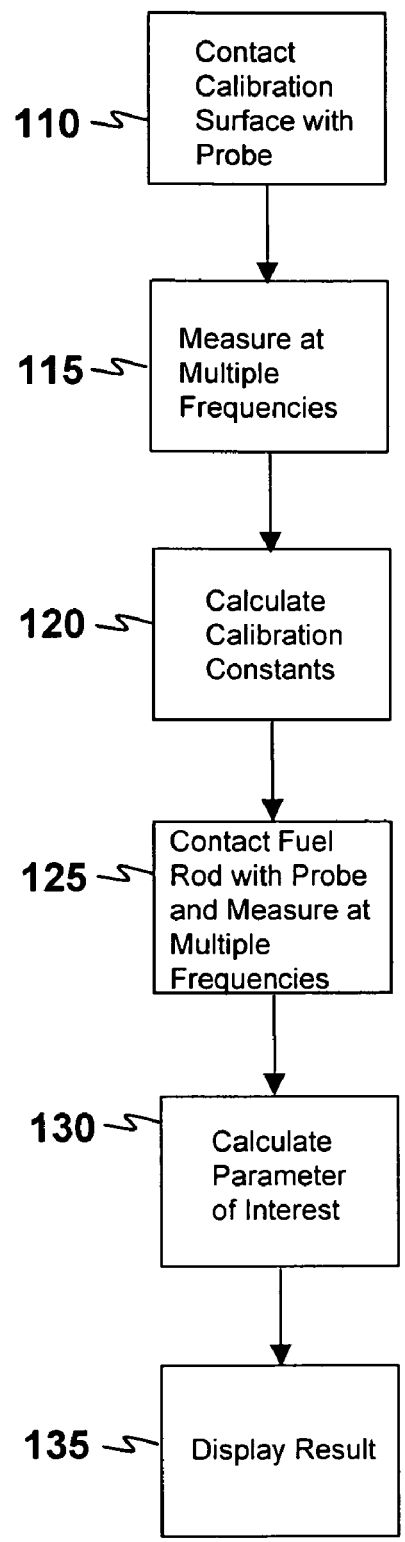
FIG. 1 is a process flow diagram according to one embodiment of the present invention.

FIG. 1 is a process flow diagram according to one embodiment of the present invention. FIG. 1 provides an overview of one embodiment of a process that may be followed to obtain a measurement of hydrogen concentration in metal. The process is described in the context of measurement of hydrogen in nuclear fuel rod claddings. In this embodiment, the fuel rods will preferably be located in a fuel storage pool, which is filled with water. However, the present invention is not limited to either the measurement of hydrogen concentration or to nuclear fuel rods, nor is it limited to use in aqueous systems or any other type of environment. The invention is also discussed in a certain order of operation. The order of operation is not critical, and the invention is not limited to the order presented.

At step 110, a probe attached to an eddy current measurement device is brought into contact with a calibration standard. The eddy current probe used in this invention is preferably a surface probe. The probe should contact the surface in a reproducible manner to prevent a decrease in sensitivity due to inadequate contact with the surface. Preferably, contacting the surface in a reproducible manner is accomplished through the use of spring-loading, which provides constant pressure sensor-to-surface contact. Additionally, the probe will preferably be oriented perpendicular to the surface of the calibration standard with little or no variation from the perpendicular direction. Also, the area(s) selected for measurement should be as similar as possible in geometry to each other. Differences in geometry such as curves, edges or other types of discontinuities may affect eddy current response and lead to errors in concentration measurement.

In addition to geometric or positioning sources of error, there are other typical material conditions that may lead to variable eddy current response that may obscure the response from the hydrogen concentration. Typical sources of background include: 1) variation in zirconium oxide thickness, (2) ferromagnetic and non ferromagnetic crud thickness, (3) variation in the crud magnetic permeability, (4) variation in hydrogen concentration across the cladding wall, and (5) variation in cladding temperature. These material conditions should be accounted for when preparing the calibration samples. These factors may be accounted for by using a calibration standard that replicates as closely as possible whichever of these factors will be present in the actual sample to be measured.

At step 115, the calibration standard is measured at a predetermined number of frequencies and locations, where each location contains a known level of the parameter of interest and representative values of the background variables. As discussed in more detail below, the calibration standard would have varying levels of the parameter of interest extending beyond the range expected in the in-situ measurements, as well as having representative levels of background variables that may affect the measurement of the sample. When measured, the eddy current probe response is dependent upon the electrical conductivity of the calibration standard, which, in turn, is dependent upon the level of the parameter of interest in the standard, such as hydrogen concentration.

Figure 2:
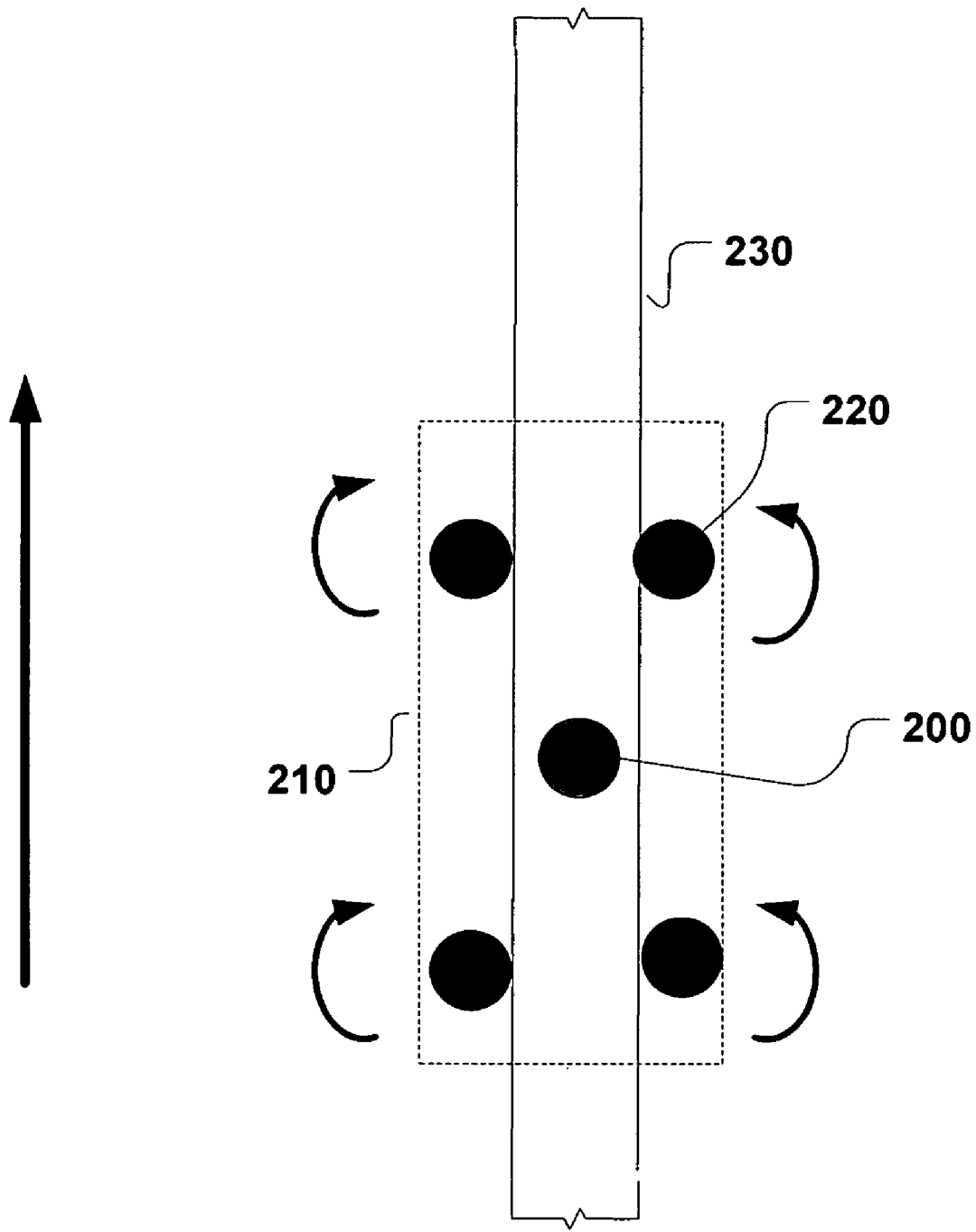
FIG. 2 is a schematic diagram of a movable probe mount and a calibration standard according to an embodiment of the invention.

FIG. 2 is a schematic diagram of a movable probe mount and a calibration standard according to an embodiment of the invention. As shown in FIG. 2, to perform the calibration in this embodiment the eddy current probe 200 is brought into contact with the surface of the calibration standard 230. The probe 200 is held using a mount 210 that allows the probe 200 to traverse the length of the calibration standard 230. The mount 210 further includes a mode of automatically traversing the calibration standard, such as wheels 220 powered by an electric motor (not shown). The purpose of the mount 210 is to allow reproducible sample-to-probe contact pressure, as well as to allow the probe 200 to be moved along the length of the sample and calibration standard 230 at a reproducible rate. The probe response from the calibration standard 230 is measured as the probe 200 moves along the standard.

In connection with the present embodiment, calibration standards are, in general, fabricated to duplicate the size, shape, and construction material of the fuel rod measured as closely as possible. In the present embodiment, the calibration standards should contain varying amounts of hydrogen, preferably encompassing the concentration range of hydrogen expected, with the exception that the standard contains no fissionable material. For instance, if the highest concentration of hydrogen expected is approximately 500 parts per million (ppm), the highest concentration standard should contain at least this concentration. Preferably, the concentration of the highest standard should be at least 25 percent more than the highest concentration expected. The distribution of the varying parameter levels in each calibration standard point is determined by routine destructive and nondestructive techniques capable of measuring hydrogen concentration, e.g., hot vacuum extraction, and imaging hydride platelets within the cladding wall, e.g., metallography.

Fuel rod cladding is often constructed of ZIRCALOY™-4 in a tubular shape. Therefore, in a preferred embodiment, the calibration standard should be constructed of ZIRCALOY™-4 material, in a tubular configuration, of approximately the same dimension as the fuel rods. Typically the cladding wall thickness is the order of 0.6 mm. Hydrogen-charged samples are prepared by any of a number of methods known to the art, such as electrochemical deposition or elevated temperature exposure of the metal standard to flowing hydrogen gas. In a preferred embodiment, the samples are prepared by flowing hydrogen gas in combination with thermal cycling. The distribution of hydrogen across the calibration standard is controlled through the application of differing temperature gradients across the standard. Alternatively, the standards may be prepared by flowing hydrogen across the standard, then subsequently applying heat in the manner described above.

The calibration standard may also be used for temperature calibration. Such a calibration standard would include a source of heat to produce the same temperature and possibly temperature gradient across the calibration standard. In an embodiment, the heat source is an internal electrical heater rod. However, any other type of suitable heat source may be used, such as a heat exchange coil or circulating water bath or heating tape attached to the calibration standard. In practice, however, it is often not necessary to perform a rigorous temperature calibration for each set of measurements. Often, it is possible to quantify the relationship between cladding temperature and eddy current response in a separate activity, such as a laboratory environment. Any temperature gradient through the cladding wall can often be accounted for analytically, or, if sufficiently small, ignored. Often, only one temperature calibration measurement is performed at the OD of the fuel rod cladding. One method of measuring temperature at the OD would be using a thermocouple, for instance.

Other variables may be generated in the calibration standards using a number of different methods known to the art. For example, $ZrO_2$ overlayers may be produced by flowing a mixture of helium and oxygen over the OD of the calibration standard while holding the standard at elevated temperatures, and magnetic shims or magnetic tapes of varying thicknesses may be used to simulate the magnetic crud overlayers.

The minimum number of frequencies to be measured at each point along the calibration standard is dependent upon the number of significant independent background variables. Each data point collected at each frequency is composed of two components, a resistance component and a reactance component (in some measurement instruments the in-phase component and the quadrature component, or the amplitude and phase angle of the response). Therefore, when N different frequencies are measured, 2N sets of data result. Generally the method can suppress the effects of 2N−1 background variables. Thus if there are three background variables, two frequencies are required. If there are five background variables, three frequencies are required. The greater the number of background variables to be suppressed the higher the data precision required.

In one embodiment, three background variables are assumed to have significant effects on the eddy current response: zirconium oxide thickness, effective crud permeability and fuel rod temperature. Thus the test must be performed at two frequencies or more, and variation in these parameters must be included in calibration data. With two frequencies there are five first order constants.

Very high test frequencies are required to reduce the sensitivity to cladding wall thickness and to increase the sensitivity to the high hydrogen concentrated near the OD. The penetration depth at a given frequency is given by the following relationship:

$$\delta = 50.3 * (\rho/(f^* \mu_r))^{1/2}$$

Here $\delta$ is the electromagnetic depth of penetration (skin depth) in mm, $\rho$ is the electrical resistivity in micro ohm cm, f is the electromagnetic frequency in Hz, and $\mu_r$ is the relative magnetic permeability. In one embodiment, one frequency may be 25 MHz, and a second frequency may be 10 MHz. At these frequencies, the depths of penetration are the order of 0.085 mm and 0.135 mm, respectively, and only approximately 15% and 25% of the ZIRCALOY™ cladding wall is penetrated.

An example calibration test matrix may include 10 or more test points. Test matrices may be derived using design of experiment techniques or through other methods known in the art. Below is a representative 15 point test matrix (in this example, "Magnetic Crud Layers" refers to a relative value proportional to the eddy current response obtained from measuring a crud layer of non-specified thickness and composition, i.e., a value of "2" represents twice the measured eddy current probe response that a value of "1" does):

| Test Point Number | Hydrogen (ppm) | ZrO$_2$ (microns) | Magnetic Crud Layers | Temperature (° C.) |
|---|---|---|---|---|
| 1 | 0 | 0 | 0 | 30 |
| 2 | 300 | 0 | 0 | 30 |
| 3 | 600 | 0 | 0 | 30 |
| 4 | 0 | 0 | 0 | 40 |
| 5 | 300 | 100 | 0 | 40 |
| 6 | 600 | 0 | 0 | 40 |
| 7 | 0 | 50 | 0 | 30 |
| 8 | 300 | 0 | 1 | 30 |
| 9 | 600 | 100 | 0 | 30 |
| 10 | 0 | 100 | 2 | 40 |
| 11 | 300 | 0 | 2 | 40 |
| 12 | 600 | 50 | 1 | 40 |
| 13 | 0 | 0 | 0 | 30 |
| 14 | 300 | 50 | 1 | 30 |
| 15 | 600 | 0 | 2 | 30 |

Returning to FIG. 1, at step 120 calibration constants are calculated based on the eddy current responses measured for the calibration standards. It should be appreciated that no mathematical model of the instrument, sensor, or the interaction of the sensor with the fuel rod and environment are assumed, nor is an iterative procedure used to determine the free parameters of a mathematical model. It is assumed that the physical parameter of interest (for example, hydrogen concentration) is dependent upon eddy-current response.

To determine the calibration constants, a Taylor Series expansion around a nominal value of the parameter of interest is performed. A description of this approach is given in Suresh Yagnik et al., Eddy Current Measurements of Corrosion and Metal Loss in Zircalloy Cladding with Ferromagnetic Crud, Nuclear Technology, Vol. 147, August 2004, p 1, which is incorporated by reference herein in its entirety. If only the first order expansion terms our included then the physical parameter of interest (PP) can be expressed as:

$$PP = A + B_1 * X_1 + C_1 * R_1 + B_2 * X_2 + C_2 * R_2 + \ldots + B_N * X_N + C_N * R_N,$$

where $A, B_1, C_1, \ldots B_N$ and $C_N$ are constants, $X_1$ and $R_1$ are the reactance and resistance at frequency 1, $X_2$ and $R_2$ are the reactance and resistance at frequency 2, and $X_N$ and $R_N$ are the reactance and resistance at frequency N. The constants can be determined if the detailed relationship between the physical parameter and the eddy current response parameters are known, or, as in a preferred embodiment, if a set of at least 2N+1 measurements are made on the calibration standard. Better results may be obtained if 4N or more measurements are made with a best fit used to determine the 2N+1 calibration constants. This approach is rigorously correct for a small range of the physical parameter measured. For a larger range, higher order terms can be included in the expansion, or the expansion can be repeated at different nominal values. However, either of these approaches requires more calibration constants and calibration measurements. The calculation may be done remotely, using a desktop computer and commercially-available software packages. Spreadsheet-based software packages such as Microsoft EXCEL™, for instance, may be adequate for many applications. Alternatively, the code may be resident in the data-handling system of the eddy current measurement device.

At step 125, once the calibration standards have been measured and the calibration constants have been calculated, the fuel rod sample is measured. In one embodiment, the outside surface temperatures of the cladding are measured using a thermocouple in contact with the outside of the fuel rod. The same sensor, eddy current instrument, cabling, test frequencies, voltage levels input to sensor, and measurement procedures as used in the calibration phase may be used.

At step 130, the parameter of interest, hydrogen concentration in this embodiment, is calculated using the calibration constants determined as described above. With the calculated constants and the values of $R_i$ and $X_i$ obtained from the sample measurements, the hydrogen concentration is calculated at each point of interest. The calculation may be done remotely using a desktop computer and commercially-available software packages. Spreadsheet-based software packages, for instance, may be adequate for many applications. Alternatively, the software code necessary to perform this calculation may be resident in the data-handling system of the eddy current measurement device and the hydrogen concentration calculated in real time.

At step 135, the calculated parameters of interest, in this embodiment hydrogen concentrations, are displayed. The display may take any form but typically comprises displaying the results on a computer screen or as a hard-copy printout.

Figure 3:
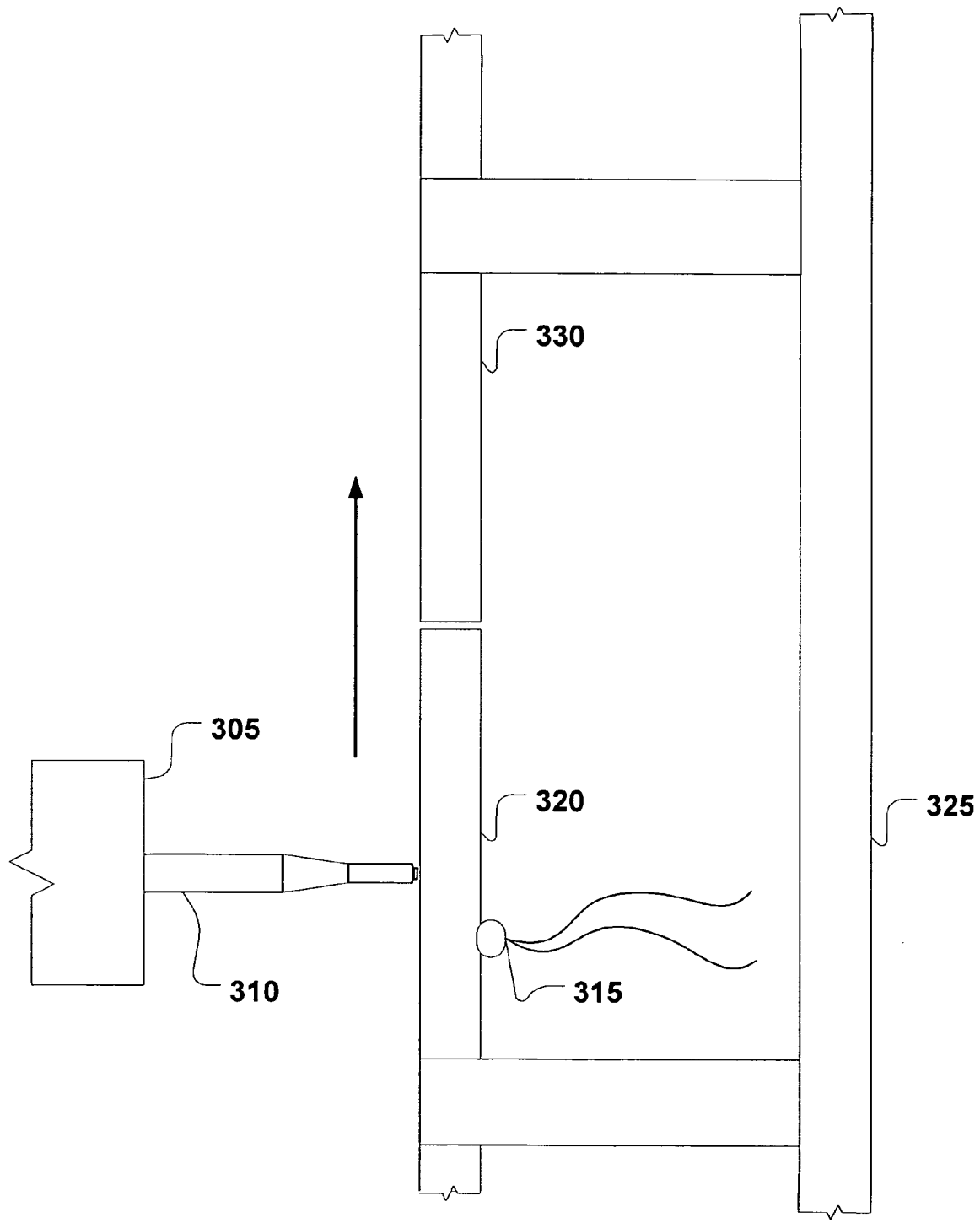
FIG. 3 is a schematic diagram of a calibration standard and a fuel rod according to one embodiment of the present invention.

FIG. 3 is a schematic diagram of a calibration standard 320 and a fuel rod 330 according to one embodiment of the invention. In this embodiment, the calibration standard 320 is immersed in a fuel storage tank (not shown) either adjacent to the tank used for the storage of nuclear fuel rods or preferably in the same tank as the one used for the storage of the nuclear fuel rods. The calibration standard 320 is held in a mechanical mount 325. The mechanical mount 325 is further configured so that it can hold a nuclear fuel rod 330 to be measured. When a measurement is made, the nuclear fuel rod 330 is transferred using a transfer means (not shown) from its storage position into the mechanical mount 325. The fuel rod 330 is positioned adjacent to and substantially in-line with the calibration standard 320 as shown in FIG. 2. An eddy current probe 310 is held in a movable probe mount 305. The eddy current probe 310 is brought into contact with the calibration standard 320. After the probe 310 is brought into contact with the surface of the calibration standard 320, the probe 310 begins traversing down the length of the calibration standard 320 while simultaneously monitoring the eddy current response at the requisite number of frequencies. The translation rate along the calibration standard 320, and ultimately the nuclear fuel rod 330, in one embodiment is approximately 160 inches/minute, although any practical rate can be used depending on the nature of probe used and the configuration of the standard and sample. It should be noted that while calibration of the present invention is performed in-situ, the present method is not restricted to in-situ calibration.

In the current embodiment, the outer surface temperature is read from a thermocouple 315 attached to the calibration standard 320. If desired or necessary, temperature calibration measurements may be done alternatively in a laboratory setting. In yet another embodiment, after a sufficient number of calibrations have been performed on a given fuel rod type, a large enough database may exist to allow for calculation of the temperature effect, thus eliminating the need for a separate temperature measurement.

Once a sufficient number of measurements have been made on the calibration standard 320, the eddy current probe 310 continues on to traverse the nuclear fuel rod 330. Less preferably, the calibration standard 320 may be removed using a remotely-controlled transfer means (not shown), and a nuclear fuel rod substituted for the calibration standard 320 in the rod mount 325. Once the nuclear fuel rod 330 is in place, the eddy current probe 310 is brought into contact with the surface of the nuclear fuel rod 330, and the probe 310 is driven along the surface of the nuclear fuel rod 330 at the same rate used for the calibration.

After completion of calibration and nuclear fuel rod data collection, calibration constants are calculated from the calibration measurements, and hydrogen concentrations for each sample point are calculated using the calibration constants and nuclear fuel rod data. After calculating the hydrogen concentrations, the results are displayed using whatever means are convenient and appropriate. Possible means include digital meter readout, analog meter readout, computer display, or operator notation. Typical units for display will be ppm hydrogen.

Although the present invention has been described with particular reference to its preferred embodiments, it should be understood that these embodiments are illustrative and that the invention may be modified and practiced in different but equivalent manners apparent to those skilled in the art having the benefit of the teachings herein. It is therefore evident that the particular embodiments disclosed above may be altered or modified in ways that such variations are considered within the scope and spirit of the invention. For example, the present invention may be utilized to measure other parameters that influence metal conductivity, such as temperature and microstructural damage from irradiation alone or in combination with parameters that influence the separation of the sensor from the metal surface, such as oxide and crud thickness. In these cases, the same methodology may be used by first calibrating the eddy current probe using a calibration standard that has known amounts of the parameter of interest and is also configured to similar the material or substrate against which the eddy current probe will be used. Therefore, the scope of the invention should not be limited by the specific disclosure herein.

What is claimed is:

1. A method for measuring hydrogen concentration in an electrically conductive material, comprising:
    calibrating an eddy current probe at a plurality of hydrogen concentrations, wherein said calibrating comprises measuring eddy currents at a plurality of positions along a calibration standard;
    measuring eddy currents at a plurality of positions along an electrically conductive material; and
    calculating a hydrogen concentration in said electrically conductive material at each of said positions along said electrically conductive material.

2. The method of claim 1, wherein said calibrating further comprises measuring said eddy currents at said plurality of positions along said calibration standard at a plurality of frequencies at each of said positions along said calibration standard.

3. The method of claim 2, wherein said plurality of frequencies is within the range 1 KHz to 40 MHz.

4. The method of claim 2, wherein said plurality of frequencies is approximately 2 to approximately 10.

5. The method of claim 2, wherein said calibrating provides a set of calibration data, and wherein said calculating comprises calculating a set of calibration constants using a Taylor series expansion based upon said set of calibration data and calculating said hydrogen concentration based upon said set of calibration constants.

6. The method of claim 1, wherein said calibration standard comprises a background variable that simulates said background variable present in said electrically conductive material.

7. The method of claim 6, wherein said background variable is selected from the group consisting of zirconium oxide thickness, crud thickness, effective crud permeability, fuel rod temperature and combinations thereof.

8. The method of claim 1, wherein said electrically conductive material is a nuclear fuel rod cladding.

9. The method of claim 1, wherein said electrically conductive material is a zirconium alloy.

10. A method for measuring hydrogen concentration in a nuclear fuel rod, comprising:
    calibrating an eddy current probe at a plurality of hydrogen concentrations along a nuclear fuel rod calibration standard disposed within a pool of water;
    measuring eddy currents at a plurality of positions along a nuclear fuel rod disposed adjacent to said nuclear fuel rod calibration standard in said pool of water; and
    calculating a hydrogen concentration in said nuclear fuel rod at each of said positions along said nuclear fuel rod.

11. The method of claim 10, wherein said calibrating further comprises measuring said eddy currents at said plurality of positions along said nuclear fuel rod calibration standard at a plurality of frequencies at each of said positions along said nuclear fuel rod calibration standard.

12. The method of claim 11, wherein said plurality of frequencies is within the range 1 KHz to 40 MHz.

13. The method of claim 11, wherein said plurality of frequencies is approximately 2 to approximately 10.

14. The method of claim 11, wherein said calibrating provides a set of calibration data, and wherein said calculating comprises calculating a set of calibration constants using a Taylor series expansion based upon said set of calibration data and calculating said hydrogen concentration based upon said set of calibration constants.

15. The method of claim 10, wherein said nuclear fuel rod calibration standard comprises a background variable that simulates said background variable present in said nuclear fuel rod.

16. The method of claim 15, wherein said background variable is selected from the group consisting of zirconium oxide thickness, crud thickness, effective crud permeability, fuel rod temperature and combinations thereof.

17. A system for measuring hydrogen concentration in a nuclear fuel rod, comprising:
    an eddy current probe for measuring eddy currents at a plurality of positions along a nuclear fuel rod;
    a nuclear fuel rod calibration standard for calibrating said eddy current probe at a plurality of hydrogen concentrations;
    a data handling system for collecting eddy current measurements generated by said eddy current probe and for calculating a hydrogen concentration at each of the plurality of positions using the eddy current measurements.

18. The system of claim 17, further comprising a mount configured to hold said nuclear fuel rod calibration standard and a nuclear fuel rod to be measured.

19. The system of claim 17, further comprising a movable probe mount configured to hold said eddy current probe and to traverse along a length of said nuclear fuel rod calibration standard and the nuclear fuel rod to be measured.

* * * * *